United States Patent
Troxell et al.

[19]

[11] Patent Number: 6,126,664
[45] Date of Patent: Oct. 3, 2000

[54] DEVICE AND METHOD FOR LOCATING AND RESECTING BONE

[75] Inventors: Thomas N. Troxell, Pottstown, Pa.; Randall M Chesnut, Portland, Oreg.

[73] Assignee: Synthes (USA), Paoli, Pa.

[21] Appl. No.: 09/232,825

[22] Filed: Jan. 19, 1999

[51] Int. Cl.[7] .................................................. A61B 17/00
[52] U.S. Cl. ............................................. 606/84; 606/87
[58] Field of Search ................................ 606/86, 79, 84, 606/87, 83; 451/378

[56] References Cited

U.S. PATENT DOCUMENTS

| | | | |
|---|---|---|---|
| D. 295,318 | 4/1988 | Gazale | D24/28 |
| 4,586,496 | 5/1986 | Keller | 128/92 E |
| 4,586,497 | 5/1986 | Dapra et al. | 128/92 |
| 4,600,005 | 7/1986 | Hendel | 128/304 |
| 4,627,425 | 12/1986 | Reese | 128/92 VY |
| 5,135,528 | 8/1992 | Winston | 606/79 |
| 5,306,278 | 4/1994 | Dahl et al. | 606/96 |
| 5,405,349 | 4/1995 | Burkinshaw et al. | 606/88 |
| 5,665,090 | 9/1997 | Rockwood et al. | 606/80 |
| 5,722,977 | 3/1998 | Wilhelmy | 606/84 |
| 5,810,649 | 9/1998 | Oar et al. | 451/378 |

FOREIGN PATENT DOCUMENTS

| | | |
|---|---|---|
| 219088 | 8/1968 | U.S.S.R. . |
| 634740 | 11/1978 | U.S.S.R. . |
| 1337-070 | 9/1987 | U.S.S.R. . |
| 1660-687 | 7/1991 | U.S.S.R. . |
| WP 91/13536 | 9/1991 | WIPO . |

*Primary Examiner*—Michael Buiz
*Assistant Examiner*—Julian W. Woo
*Attorney, Agent, or Firm*—Pennie & Edmonds LLP

[57] ABSTRACT

A device and method for the location of a pedicle and resection of the corresponding lamina are disclosed. The device includes an osteotome having a cutting element configured and dimensioned to remove a section of bone sized to accommodate a portion of an implant; and a pedicle finder having a handle at a proximal end for manipulation of the pedicle finder, a pedicle locator at a distal end connected to the handle by a shaft, and a osteotome guide located on the shaft configured and dimensioned to slidingly engage at least a portion of the osteotome. By providing the osteotome guide on the same device as the pedicle locator and configuring the cutting element of the osteotome and osteotome guide to remove a fixed section of bone, the size and position of the resected bone is optimized to help ensure proper seating of an implant such as a pedicle hook.

19 Claims, 1 Drawing Sheet

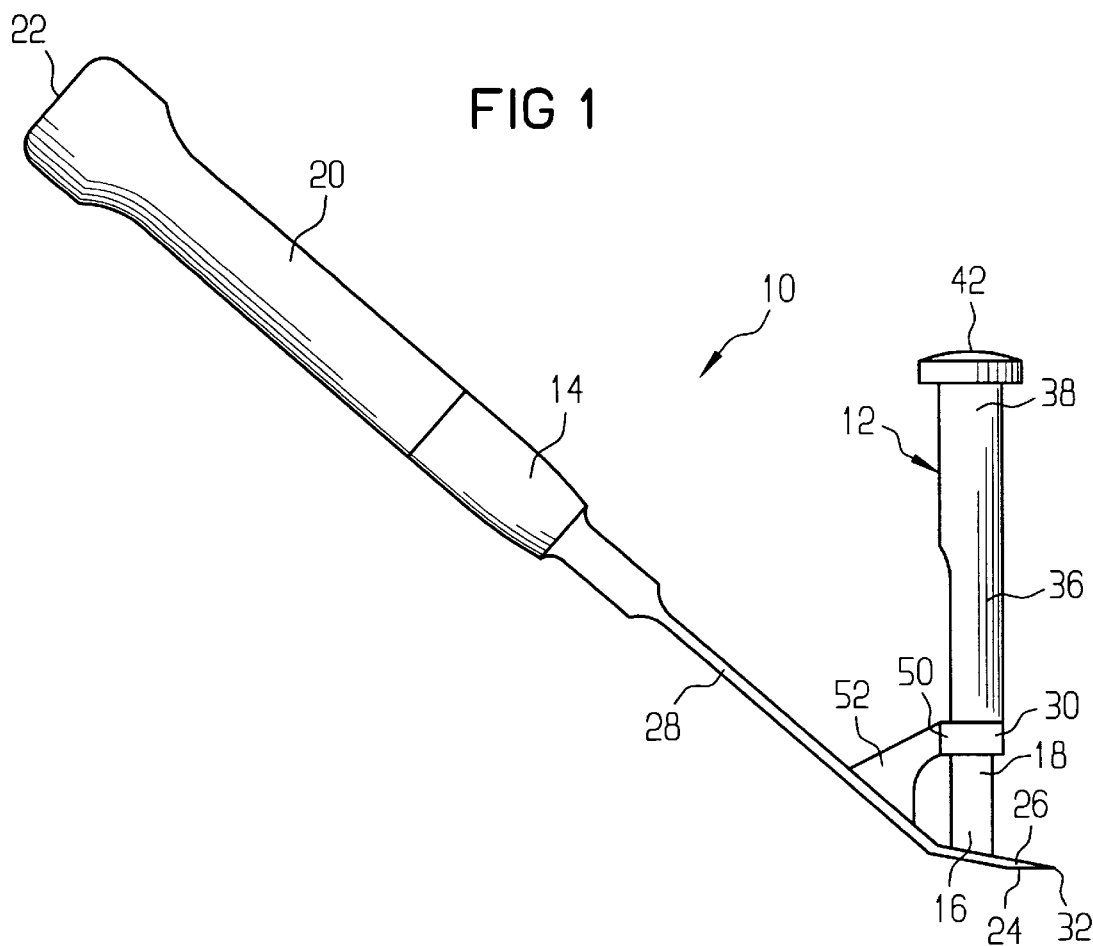
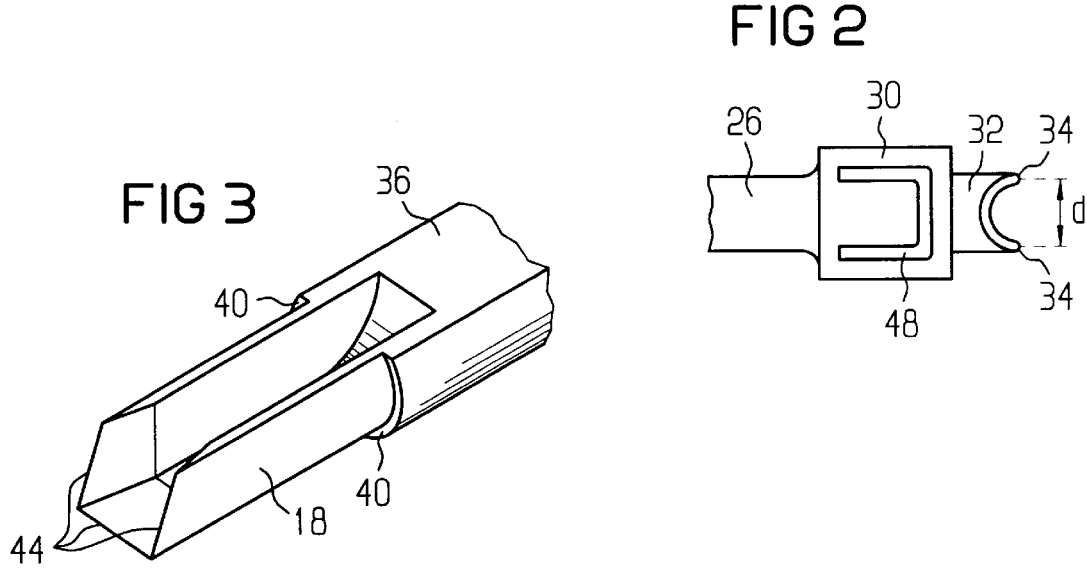

DEVICE AND METHOD FOR LOCATING AND RESECTING BONE

FIELD OF THE INVENTION

The present invention is directed to a device and method for locating and resecting a section of bone, and in particular to a surgical tool and method for locating and resecting a section of a lamina of a spine to create a space for insertion of a pedicle hook.

BACKGROUND OF THE INVENTION

It is often necessary to surgically treat spinal deformities. Numerous systems for use in spinal correction and fixation have been disclosed. Although there are a number of factors which determine the system utilized in a given clinical situation, surgical approach, i.e. anterior, posterior, or lateral, significantly influences system selection. Posterior systems usually include one or more longitudinal rods placed generally parallel to the spinous process with various attachment devices connecting the rod and a selected component of the spine. These attachment devices include pedicle screws, plates, spinous process hooks, sublaminar hooks, and pedicle hooks.

With respect to the use of hooks, the hooks should be pressed firmly against the bone to properly transfer stress from the spine to the longitudinal rod. In order to accomplish correct seating of a pedicle hook, a section of the lamina is typically removed. However, anatomical considerations make removal of the appropriate section of laminar bone difficult to determine. Consequently, the seating of a pedicle hook can be a complex task.

Synthes USA of Paoli, Pa. offers a pedicle finder that has etched markings on its shaft to provide the surgeon with a visual guide for freehand resection of bone from the lamina after the pedicle has been located. Sofamor Danek, Inc. of Memphis, Tenn., offers a pedicle elevator that assists the implantation of a pedicle hook. The pedicle elevator is used only after a portion of the lamina is resected freehand based on anatomical landmarks. With freehand resection of the lamina, frequently the distance from the cut to the pedicle is either somewhat shorter or longer than the similar distance in the pedicle hook.

Thus, there exists a need for an improved device and method for precisely locating a pedicle and resecting a portion of a lamina so that a pedicle hook can be properly implanted.

SUMMARY OF THE INVENTION

The present invention relates to a device for locating and resecting a section of bone. The device comprises an osteotome having a distal end provided with a cutting element configured and dimensioned to remove a section of bone sized to accommodate a portion of an implant; and a pedicle finder having a handle at a proximal end for manipulation of the device, a pedicle locator at a distal end connected to the handle by a shaft, and a osteotome guide located on the shaft configured and dimensioned to slidingly engage at least a portion of the osteotome. When there is impaction of the osteotome after the pedicle locator has been positioned against bone, at least a portion of the osteotome slidingly engages the osteotome guide so that the cutting element removes the section of bone.

Preferably, the pedicle locator comprises a blade having two prongs separated by a distance which is approximately equal to a width of a pedicle and the blade is tapered with a curved end. The pedicle locator can be disposed at an angle with respect to the shaft.

In another preferred embodiment, the osteotome has a collar limiting the portion of the osteotome slidingly engaged by the osteotome guide. A proximal end of the osteotome has a striking surface for impaction.

In another preferred embodiment, the cutting element of the osteotome includes at least one sharpened edge forming a u-shaped cavity. Preferably, the sharpened edge is slanted. The osteotome guide has a u-shaped slot for slidingly engaging the cutting element of the osteotome. The slot can be located on a guide housing which is connected to the shaft by a neck.

The present invention also relates to a method for removing a section of bone comprising the steps of locating an inferior side of a pedicle with a device having a pedicle locator; sliding a portion of an osteotome through an osteotome guide, said osteotome guide located on the device; and impacting a osteotome to further move the osteotome through the osteotome guide and resect the section of bone.

BRIEF DESCRIPTION OF THE DRAWINGS

FIG. 1 is a side view of the device according to the present invention;

FIG. 2 is a top view of a portion of a distal end of an osteotome guide and pedicle locator according to the present invention; and FIG. 3 is perspective view of a portion of a distal end of an osteotome according to the present invention.

DESCRIPTION OF THE PREFERRED EMBODIMENTS

As shown in FIG. 1, a device 10 for removing a section of bone according to the present invention comprises an osteotome 12 and a pedicle finder 14. A distal end 16 of osteotome 12 has a cutting element 18 configured and dimensioned to remove a section of a lamina so that a pedicle hook can be firmly seated in the thoracic or lumbar spine. It should be understood that even though accepted current medical practice limits the use of pedicle hooks to the thoracic and lumbar regions of the spine and device 10 has been designed for such pedicle hooks, device 10 can be used in other regions of the spine should standard medical practice change. It should be further understood that device 10 can be used to remove bone in areas other than the spine.

Pedicle finder 14 has a handle 20 on a proximal end 22 connected to a pedicle locator 24 on a distal end 26 by a shaft 28. Pedicle finder 14 also includes an osteotome guide 30 located on shaft 28 and configured and dimensioned so that at least a portion of osteotome 12 slides through osteotome guide 30. In use, when pedicle locator 24 contacts the inferior side of the pedicle, osteotome guide 30 is positioned such that when osteotome 12 is inserted in osteotome guide 30, a section of the lamina is resected. This section is sized and located so that the blade or hook portion of a pedicle hook could be properly seated.

FIG. 2 shows that pedicle locator 24 comprises a blade 32 having two prongs 34. Prongs 34 are separated by a distance d which is approximately equal to the width of the pedicle. In order to facilitate placement of pedicle locator 24, blade 32 is tapered and has a curved end. Pedicle locator 24 is disposed at an angle with respect to shaft 28. One way of orienting pedicle locator 24 at an angle with respect to shaft 28 is to bend shaft 28. An angle of 30° is preferred.

Referring now to FIGS. 1 and 3, osteotome 12 has a body 36 and a proximal end 38 in addition to cutting element 18. Body 36 includes a collar 40 which limits the portion of osteotome 12 that slides through osteotome guide 30. Proximal end 38 includes a striking surface 42 for impaction with a surgical tool such as hammer to provide the force so that cutting element 18 can resect bone. Cutting element 18 of osteotome 12 has at least one sharpened edge 44 which forms a u-shaped cavity. Sharpened edges 44 are slanted to facilitate resection of bone. As seen in FIG. 2, a u-shaped slot 48 on osteotome guide 30 allows cutting element 18 to slide in osteotome guide 30. Slot 48 is located on a guide housing 50. Guide housing 50 is connected to shaft 28 by a neck 52 in such a manner so that guide housing 50 is substantially parallel to pedicle locator 24.

According to the method of the present invention, after the segment of the spine to be instrumented has been exposed using the standard posterior approach, the surgeon locates an inferior side of the pedicle that will receive a pedicle hook. With the pedicle locator still in contact with the pedicle, the surgeon uses a hammer to drive the cutting element of an osteotome through an osteotome guide to remove a section of the lamina of the vertebral body. By providing the osteotome guide on the same device as the pedicle locator and configuring the cutting element of the osteotome (and osteotome guide) to remove a fixed section of bone, the size and position of the resected laminar bone is optimized to help ensure proper seating of the pedicle hook.

While it is apparent that the illustrative embodiments of the invention herein disclosed fulfill the objectives stated above, it will be appreciated that numerous modifications and other embodiments may be devised by those skilled in the art. Therefore, it will be understood that the appended claims are intended to cover all such modifications and embodiments which come within the spirit and scope of the present invention.

What is claimed is:

1. A device for removing a section of bone comprising:
   an osteotome having a distal end provided with a cutting element configured and dimensioned to remove a section of bone sized to accommodate a portion of an implant; and
   a pedicle finder having a handle at a proximal end for manipulation thereof, a pedicle locator at a distal end connected to the handle by a shaft, and a osteotome guide located on the shaft configured and dimensioned to slidingly engage at least a portion of the osteotome, wherein impaction of the osteotome after the pedicle locator has been positioned against bone causes the at least a portion of the osteotome to slidingly engage the osteotome guide so that the cutting element removes the section of bone.

2. The device of claim 1 wherein the pedicle locator comprises a blade having two prongs separated by a distance which is approximately equal to a width of a pedicle.

3. The device of claim 2 wherein the blade is tapered.

4. The device of claim 2 wherein the blade has a curved end.

5. The device of claim 1 wherein the pedicle locator is disposed at an angle with respect to the shaft.

6. The device of claim 1 wherein the osteotome has a collar limiting the portion of the osteotome slidingly engaged by the osteotome guide.

7. The device of claim 1 wherein a proximal end of the osteotome has a striking surface for impaction.

8. The device of claim 1 wherein the cutting element of the osteotome includes at least one sharpened edge forming a u-shaped cavity.

9. The device of claim 8 wherein the osteotome guide has a u-shaped slot for slidingly engaging the cutting element of the osteotome.

10. The device of claim 9 wherein the slot is located on a guide housing, said guide housing connected to the shaft by a neck.

11. The device of claim 8 wherein the at least one sharpened edge is slanted.

12. A method for removing a section of bone comprising the steps of:
    locating an inferior side of a pedicle with a device having a pedicle locator;
    sliding a portion of an osteotome through an osteotome guide, said osteotome guide located on the device; and
    impacting a osteotome to further move the osteotome through the osteotome guide and resect the section of bone.

13. The method of claim 12 wherein the pedicle locator has a blade with two prongs separated by a distance, said distance approximately a width of a pedicle.

14. The method of claim 13 wherein the blade of the pedicle locator is tapered and has a curved end.

15. The method of claim 12 wherein the pedicle locator is disposed at an angle with respect to a shaft of the device.

16. The method of claim 12 further comprising the step of limiting the movement of the osteotome to limit bone removal.

17. The method of claim 12 further comprising the step of providing the osteotome with a cutting element having at least one sharpened edge forming a u-shaped cavity.

18. The method of claim 17 further comprising the step of providing the osteotome guide with a u-shaped slot sized for sliding engagement of the cutting element of the osteotome.

19. The method of claim 17 wherein the at least one sharpened edge is slanted.

* * * * *